(12) United States Patent
Ohishi

(10) Patent No.: US 10,052,074 B2
(45) Date of Patent: Aug. 21, 2018

(54) X-RAY DIAGNOSTIC APPARATUS

(71) Applicant: Toshiba Medical Systems Corporation, Otawara-shi (JP)

(72) Inventor: Satoru Ohishi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 182 days.

(21) Appl. No.: 15/091,899

(22) Filed: Apr. 6, 2016

(65) Prior Publication Data
US 2016/0302744 A1    Oct. 20, 2016

(30) Foreign Application Priority Data

Apr. 15, 2015 (JP) ................. 2015-083675

(51) Int. Cl.
*A61B 6/08* (2006.01)
*A61B 6/00* (2006.01)
*A61B 6/06* (2006.01)

(52) U.S. Cl.
CPC ............ *A61B 6/4014* (2013.01); *A61B 6/487* (2013.01); *A61B 6/504* (2013.01); *A61B 6/5205* (2013.01); *A61B 6/54* (2013.01); *A61B 6/587* (2013.01); *A61B 6/06* (2013.01); *A61B 6/4035* (2013.01); *A61B 6/4441* (2013.01); *A61B 6/482* (2013.01)

(58) Field of Classification Search
CPC ..... A61B 6/4014; A61B 6/4021; A61B 6/487; A61B 6/504; A61B 6/5205; A61B 6/54; A61B 6/587; A61B 6/06; A61B 6/4035; A61B 6/4441; A61B 6/482
See application file for complete search history.

(56) References Cited

U.S. PATENT DOCUMENTS

| 7,246,943 | B2 | 7/2007 | Gotoh | |
| 2005/0195945 | A1* | 9/2005 | Gotoh | A61B 6/4014 378/197 |
| 2015/0272520 | A1 | 10/2015 | Kobayashi et al. | |

FOREIGN PATENT DOCUMENTS

| JP | 4703119 | 6/2011 |
| JP | 2014-138837 | 7/2014 |

* cited by examiner

*Primary Examiner* — Courtney Thomas
(74) *Attorney, Agent, or Firm* — Oblon, McClelland, Maier & Neustadt, L.L.P.

(57) ABSTRACT

An X-ray diagnostic apparatus according to an embodiment includes a first imaging system, a second imaging system, and processing circuitry. The first imaging system holds a first X-ray tube and a first X-ray detector in a rotatable manner. The second imaging system holds a second X-ray tube and a second X-ray detector in a rotatable manner, and rotating centers, which are capable to set independently, between the first imaging system and the second imaging system. The processing circuitry makes a rotating center of the first imaging system and the rotating center of the second imaging system substantially equivalent to each other when a rotation imaging program using the first imaging system and the second imaging system is selected.

20 Claims, 8 Drawing Sheets

X-RAY DIAGNOSTIC APPARATUS

CROSS-REFERENCE TO RELATED APPLICATIONS

This application is based upon and claims the benefit of priority from Japanese Patent Application No. 2015-083675, filed on Apr. 15, 2015, the entire contents of all of which are incorporated herein by reference.

FIELD

An embodiment described herein relates generally to an X-ray diagnostic apparatus.

BACKGROUND

An X-ray diagnostic apparatus is used not only for diagnosis but also for interventional treatment for cerebral aneurysm and other diseases. A vascular structure of the head is complicated and it is difficult to understand the vascular structure by simple observation from one direction in some cases. For this reason, a biplane X-ray diagnostic apparatus including a first imaging system and a second imaging system and capable of imaging from two directions simultaneously is a system suitable for diagnosis and treatment for the head and neck.

DETAILED DESCRIPTION

Hereinafter, an X-ray diagnostic apparatus according to embodiments will be described with reference to the accompanying drawings. The X-ray diagnostic apparatus in the embodiments is a biplane X-ray diagnostic apparatus including a first imaging system and a second imaging system. Embodiments are not limited to the following embodiments. Contents as described in one embodiment are applied to other embodiments in the same manner in principle.

An X-ray diagnostic apparatus according to an embodiment includes a first imaging system, a second imaging system, and processing circuitry. The first imaging system holds a first X-ray tube and a first X-ray detector in a rotatable manner. The second imaging system holds a second X-ray tube and a second X-ray detector in a rotatable manner, and it is capable to set rotating centers of the first imaging system and second imaging system independently. The processing circuitry makes the rotating center of the first imaging system and the rotating center of the second imaging system substantially identical to each other when a rotation imaging program using the first imaging system and the second imaging system simultaneously is selected from a user.

First Embodiment

Figure 1:
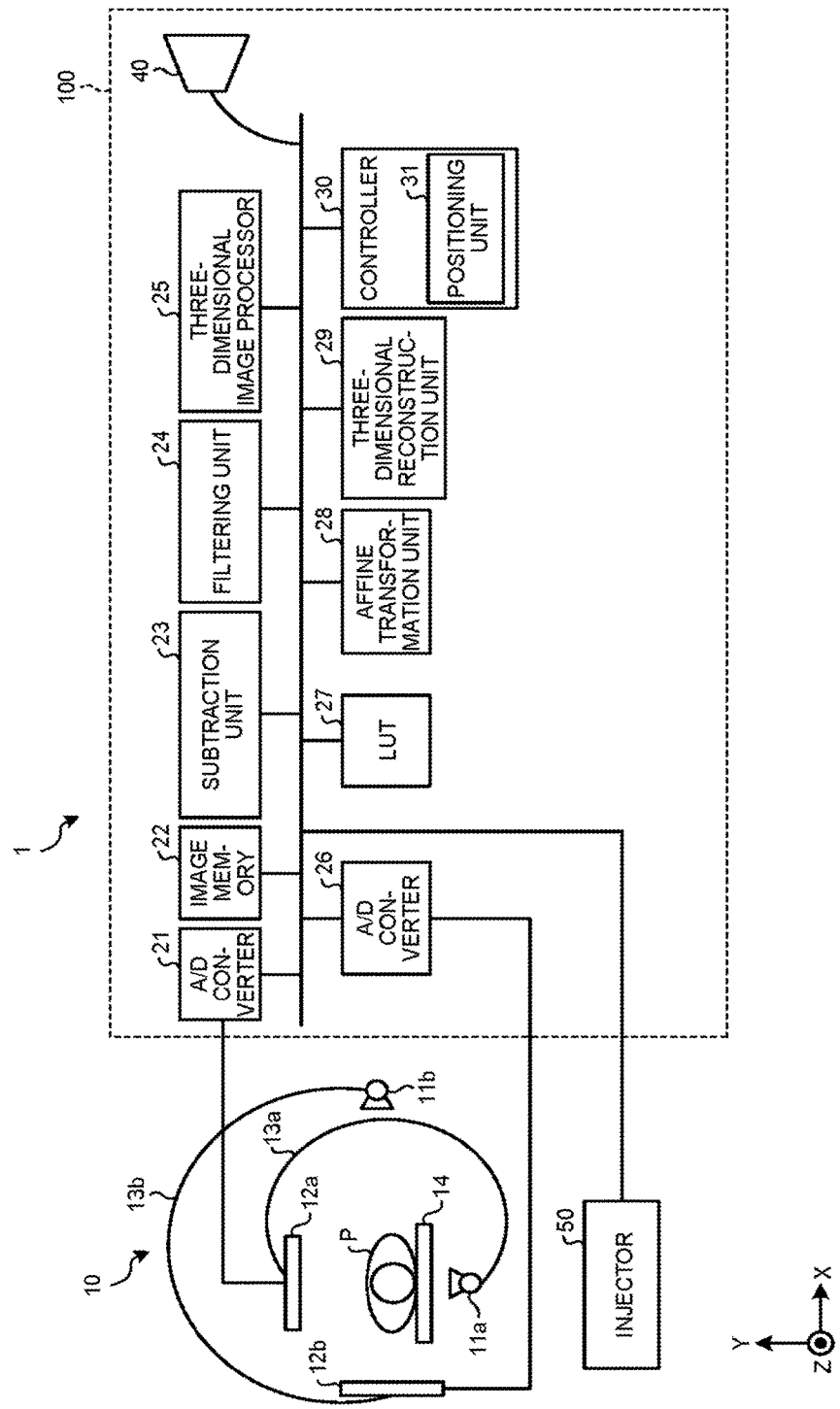
FIG. 1 is an exemplary block diagram illustrating an example of the configuration of an X-ray diagnostic apparatus according to a first embodiment.

First, the configuration of an X-ray diagnostic apparatus according to a first embodiment will be described. FIG. 1 is a block diagram illustrating an example of the configuration of an X-ray diagnostic apparatus 1 in the first embodiment. The X-ray diagnostic apparatus 1 does not include a subject P (for example, human body). The configuration as illustrated in FIG. 1 is merely an example. For example, units as illustrated in FIG. 1 may be configured to be appropriately integrated or separated.

As illustrated in FIG. 1, the X-ray diagnostic apparatus 1 in the first embodiment includes an X-ray imaging mechanism 10 and an image processing device 100. The X-ray imaging mechanism 10 is a biplane imaging mechanism including a first imaging system and a second imaging system. The first imaging system includes an X-ray tube 11a (also called first X-ray tube 11a), an X-ray detector 12a (also called first X-ray detector 12a), and a C-shaped arm 13a and the second imaging system includes an X-ray tube 11b (also called second X-ray tube 11b), an X-ray detector 12b (also called second X-ray detector 12b), and an Ω-shaped arm 13b. The first imaging system and the second imaging system are controlled independently because a medical doctor does not always check the same region by the first imaging system and the second imaging system. In other words, a rotating center of the first imaging system and a rotating center of the second imaging system are located independently in most cases. With this independent control, the medical doctor can observe different regions by the first imaging system and the second imaging system. For example, the medical doctor can see an intracranial portion with the first imaging system mainly and check cervical regions with the second imaging system. The independent rotating centers of the first imaging system and the second imaging system as described above enable flexible imaging.

The X-ray imaging mechanism 10 includes a couch 14 and an injector 50 is connected thereto. The couch 14 is a bed on which the subject P is placed. In the X-ray imaging mechanism 10, a three-dimensional orthogonal coordinate system formed by an X axis, a Y axis, and a Z axis is defined, as illustrated in FIG. 1. That is to say, the X axis indicates the horizontal direction, the Y direction indicates the vertical direction, and the Z axis indicates a body-axis direction of the subject P. In the three-dimensional orthogonal coordinate system, directions as indicated by arrows are set to positive directions.

Each of the X-ray tube 11a and the X-ray tube 11b is a device generating X rays using a high voltage that is supplied from a high voltage generator (not illustrated).

Each of the X-ray detector 12a and the X-ray detector 12b is a flat panel detector (FPD) or an image intensifier (I.I.), for example. Each of the X-ray detector 12a and the X-ray detector 12b is a device in which X-ray detecting elements for detecting X rays that have transmitted through the subject P are aligned in a matrix form and the X-ray detecting elements convert the X rays that have transmitted through the subject P to electric signals (X-ray signals), accumulate the converted electric signals, and store the accumulated electric signals in an image memory 22, which will be described later. It should be noted that the X-ray signals converted by the X-ray detector 12a are referred to as first X-ray signals and the X-ray signals converted by the X-ray detector 12b are referred to as second X-ray signals.

The C-shaped arm 13a is an arm holding the X-ray tube 11a and the X-ray detector 12a. The X-ray tube 11a and the X-ray detector 12a are arranged so as to oppose each other with the subject P interposed therebetween by the C-shaped arm 13a. The C-shaped arm 13a supports the X-ray tube 11a and the X-ray detector 12a, and rotates around the subject P lying on the couch 14 like a propeller at high speed by a motor provided on a supporting portion (not illustrated). The C-shaped arm 13a is supported in a rotatable manner about the orthogonal three axes of the X axis, the Y axis, and the Z axis, and individually rotates about each axis by a driving unit (not illustrated).

The Ω-shaped arm 13b is an arm holding the X-ray tube 11b and the X-ray detector 12b. The X-ray tube 11b and the X-ray detector 12b are arranged so as to oppose each other with the subject P interposed therebetween by the Ω-shaped arm 13b. The Ω-shaped arm 13b supports the X-ray tube 11b and the X-ray detector 12b, and rotates around the subject P lying on the couch 14 by a motor provided on a supporting portion (not illustrated) suspended from a ceiling rail. The Ω-shaped arm 13b is supported in a rotatable manner about the orthogonal three axes of the X axis, the Y axis, and the Z axis, and individually rotates about each axis by a driving unit (not illustrated).

The injector 50 is a device for injecting a contrast agent through a catheter inserted into the subject P. Start of the injection of the contrast agent from the injector 50 may be executed based on an injection start instruction received through the image processing device 100, which will be described later, or may be executed based on an injection start instruction that a user such as the medical doctor has directly input to the injector 50.

The X-ray imaging mechanism 10 configured as described above is controlled by a imaging controller (not illustrated). For example, the imaging controller controls various types of processing related to imaging by the X-ray imaging mechanism 10 under control by a controller 30, which will be described later. For example, the imaging controller controls rotation imaging of collecting pieces of projection data at a predetermined frame rate while rotating the C-shaped arm 13a or the Ω-shaped arm 13b. As an example, the imaging controller outputs a signal for instructing the injector 50 to start injection of the contrast agent and controls the rotation imaging a plurality of times after the single injection of the contract agent. Furthermore, the imaging controller controls the high voltage generator (not illustrated) so as to generate X-rays continuously or intermittently from the X-ray tube 11a or the X-ray tube 11b and detect the X-rays that have transmitted through the subject P on the X-ray detector 12a or the X-ray detector 12b the X rays while controlling rotation of the C-shaped arm 13a or the Ω-shaped arm 13b.

As illustrated in FIG. 1, the image processing device 100 includes an analog/digital (A/D) converter 21, the image memory 22, a subtraction unit 23, a filtering unit 24, a three-dimensional image processor 25, an A/D converter 26, a look up table (LUT) 27, an affine transformation unit 28, a three-dimensional reconstruction unit 29, the controller 30, and a display unit 40. The image processing device 100 includes an input unit that receives various types of operations on the X-ray diagnostic apparatus 1 from the user, although the input unit such as a mouse, a keyboard, a trackball, and a pointing device is not illustrated in FIG. 1.

The display unit 40 displays various types of images that have been processed by the image processing device 100 and various types of information such as a graphical user interface (GUI). For example, the display unit 40 is a cathode ray tube (CRT) monitor or a liquid crystal monitor. The A/D converter 21 is connected to the X-ray detector 12a, converts analog signals input from the X-ray detector 12a to digital signals, and stores the converted digital signals in the image memory 22 as X-ray images. The A/D converter 26 is connected to the X-ray detector 12b, converts analog signals input from the X-ray detector 12b to digital signals, and stores the converted digital signals in the image memory 22 as X-ray images.

The image memory 22 stores therein the X-ray images (pieces of projection data). For example, the image memory 22 stores therein the pieces of projection data collected by the first imaging system and the pieces of projection data collected by the second imaging system. The image memory 22 stores therein reconstructed data (volume data) reconstructed by the three-dimensional reconstruction unit 29, which will be described later, and a three-dimensional image generated by the three-dimensional image processor 25. Furthermore, the image memory 22 stores therein subtraction images generated by the subtraction unit 23, which will be described later.

The subtraction unit 23 generates the subtraction images. For example, the subtraction unit 23 generates the subtraction images between projection images collected by imaging the subject P in a rotation manner before the injection of the contract agent and projection images collected by imaging the subject P in the rotation manner after the injection of the contract agent. The first projection images and second projection images are called as mask and contrast images, respectively. To be more specific, the subtraction unit 23 generates the DSA images using pieces of mask images and contrast images collected from substantially the same directions that have been stored in the image memory 22.

The filtering unit 24 performs high-pass filtering, low-pass filtering, band-pass filtering and other operations. The LUT 27 performs gradation conversion. The affine transformation unit 28 performs zooming, minification, shift, rotation and the like.

The three-dimensional reconstruction unit 29 reconstructs reconstructed data (hereinafter, referred to as three-dimensional image data or volume data) from the pieces of projection data collected by the rotation imaging by the X-ray imaging mechanism 10. For example, the three-dimensional reconstruction unit 29 uses, as the pieces of projection data, the subtraction images that have been generated by subtracting the mask images and the contrast images by the subtraction unit 23 and stored in the image memory 22 and reconstructs the volume data from the pieces of subtraction data. Alternatively, the three-dimensional reconstruction unit 29 uses, as the pieces of projection data, the mask images and the contrast images stored in the image memory 22 and reconstructs the pieces of volume data from the pieces of projection data separately. Then, the three-dimensional reconstruction unit 29 stores the pieces of reconstructed volume data in the image memory 22. The subtraction unit 23 subtracts the two pieces of reconstructed volume data so as to generate volume data that is substantially the same as the volume data reconstructed from the subtraction images.

The three-dimensional reconstruction unit 29 in the first embodiment reconstructs the volume data using the subtraction images generated by the subtraction unit 23 based on the mask images and the contrast images collected by the first imaging system and the subtraction images generated by the subtraction unit 23 based on the mask images and the contrast images collected by the second imaging system. That is to say, the three-dimensional reconstruction unit 29 reconstructs the volume data using two-dimensional X-ray images collected from the two imaging systems. It should be noted that generation of the above-described volume data will be described later.

The three-dimensional image processor 25 generates a three-dimensional image from the volume data stored in the image memory 22. For example, the three-dimensional image processor 25 generates a volume rendering image, a surface rendering image, a minimum-intensity projection (MIP) image or a multi planar reconstruction (MPR) image from the volume data. Then, the three-dimensional image processor 25 stores the generated three-dimensional image in the image memory 22.

The controller 30 controls the entire X-ray diagnostic apparatus 1. To be specific, the controller 30 controls various types of processing related to imaging of the X-ray images by the X-ray imaging mechanism 10. For example, various types of processing are image reconstruction, generation of a display image, and display of the display image on the display unit 40. The controller 30 receives selection of a rotation imaging program from the input unit. The controller 30 includes a positioning unit 31, which will be described later.

For example, the image memory 22 is a semiconductor memory element such as a random access memory (RAM) and a flash memory or a storage device such as a hard disc and an optical disc. Each of the subtraction unit 23, the filtering unit 24, the three-dimensional image processor 25, the LUT 27, the affine transformation unit 28, the three-dimensional reconstruction unit 29, and the controller 30 is an electronic circuit such as a central processing unit (CPU) and a micro processing unit (MPU) or an integrated circuit such as an application specific integrated circuit (ASIC) and a field programmable gate array (FPGA), for example.

The X-ray diagnostic apparatus 1 configured as described above is used for interventional treatment, which will be described below, for example. In the interventional treatment, devices including a guide wire and a catheter are inserted from a groin or other regions of the subject P. Then, treatment devices are delivered to a diseased part for treatment via the inserted devices (for example, embolization with coil or expansion with a balloon or a stent).

When the medical doctor operates the catheter and the guide wire, for example, the medical doctor sets the first imaging system in front of the subject P and sets the second imaging system along the side of the subject P. That is to say, the first imaging system and the second imaging system generate images with parallax of 90 degrees. The medical doctor operates the catheter and the guide wire while observing the image from the first imaging system and the image from the second imaging system. In a situation where the medical doctor has difficulty in operating the catheter and the guide wire on a certain vascular bifurcation, for example, the medical doctor changes view angles of the first imaging system and the second imaging system so that the medical doctor can easily observe the vascular bifurcation, and then the medical doctor operates the catheter and the guide wire.

It is not, however, easy to change view angles of the first imaging system and the second imaging system so that the medical doctor can easily observe the vascular bifurcation. For example, a physician with considerable experience grasps easy-to-observe angles to some extent for each vascular bifurcation in some cases. In such a case, the medical doctor can rotate the first imaging system and the second imaging system to the easy-to-observe angles. A physician with limited experience does not, however, know appropriate angles for the first imaging system and the second imaging system in many cases. In addition to individual differences in vascular structures, when a trouble such as stenosis is generated in the vascular bifurcation, it is difficult even for the physician with considerable experience to determine the appropriate angles for the first imaging system and the second imaging system in some cases.

In this case, by using a three-dimensional roadmap formed by generating a three-dimensional vascular image based on three-dimensional image data and superimposing the three-dimensional vascular image on a fluoroscopic image, the medical doctor can recognize three-dimensional structures of blood vessels and easily operate the catheter and the guide wire. The conventional three-dimensional roadmap, however, requires the following procedures for collecting the three-dimensional image data.

First, the medical doctor moves the second imaging system away from the first imaging system. The medical doctor confirms that the first imaging system does not interfere in the subject P and the couch 14 during rotation, and then, moves the injector 50 to the vicinity of the couch 14. Subsequently, the medical doctor connects the catheter to the injector 50 and sets injection conditions on the injector 50.

Before and after the injector 50 is driven and the contrast agent is injected into the subject P, the medical doctor activates rotation imaging using the first imaging system at high speed so as to collect the pieces of X-ray image data and generate a three-dimensional image. Thereafter, the medical doctor checks a state of the subject P, disconnects the catheter from the injector 50, and moves the injector 50 away from the couch 14. Then, the medical doctor sets the second imaging system to imaging position for the subject P, again.

It usually takes five minutes or more to collect the pieces of X-ray image data for three-dimensional image data in this manner. That is to say, the creation of three-dimensional image data increases an amount of the contract agent, increases exposure dose to the subject P, and interrupts the procedure for five minutes or more.

The rotation imaging using the first imaging system and the second imaging system has advantages that imaging time can be shortened or the second imaging system is not required to move away and reset. The rotating centers of the first imaging system and the second imaging system can be set independently. The medical doctor therefore needs to check imaging regions for the first imaging system and the second imaging system independently before the rotation imaging using the first imaging system and the second imaging system simultaneously. For example, the medical doctor fluoroscopically views a target at a certain angle $\theta$ and an another angle $(\theta+90)$ or $(\theta-90)$ of a rotation imaging range for the first imaging system and fluoroscopically views the target at an another certain angle φ and an another angle (φ+90) or (φ−90) of a rotation imaging range for the second imaging system in the same manner. With this process, the medical doctor confirms the target regions so that the first imaging system and the second imaging system are not out of the field of view. Because of these situations, conventionally, operators such as the medical doctor unlikely use the three-dimensional roadmap for the purpose of supporting an operation of the catheter and the guide wire.

To get three-dimensional roadmap in shorter time with the X-ray diagnostic apparatus 1 in the first embodiment, for example, the rotating center of the first imaging system and the rotating center of the second imaging system are made substantially identical to each other when a rotation imaging program using the first imaging system and the second imaging system is selected. For example, the X-ray diagnostic apparatus 1 sets the first imaging system in front of the subject P and sets the second imaging system along the side of the subject P, and rotates the imaging systems simultaneously with keeping the rotating centers of the two imaging systems substantially identical to each other.

Figure 2:
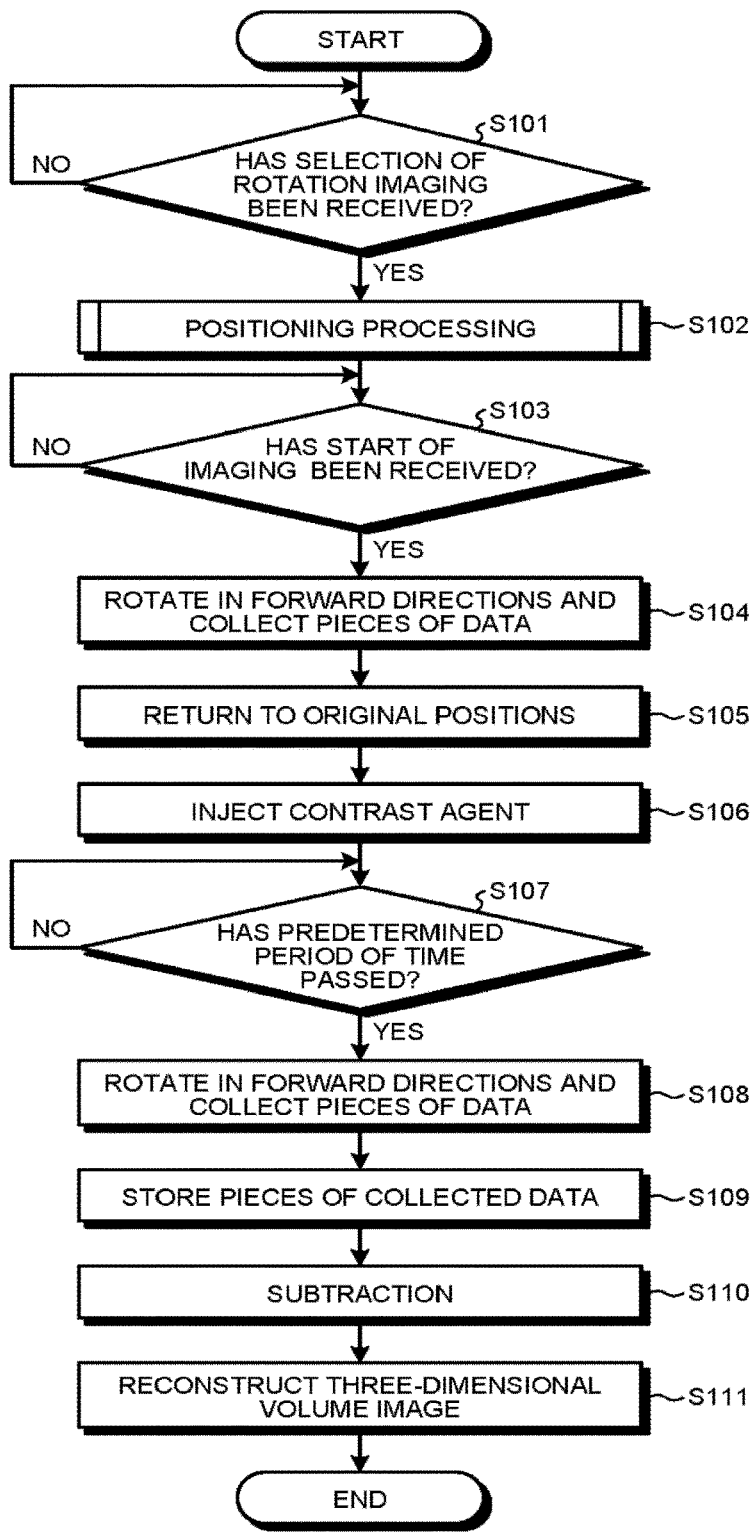
FIG. 2 is an exemplary flowchart illustrating an example of procedures of processing performed by the X-ray diagnostic apparatus in the first embodiment.

Hereinafter, an example of processing performed by the X-ray diagnostic apparatus 1 in the first embodiment will be described with reference to FIG. 2. FIG. 2 is a flowchart illustrating an example of procedures of the processing performed by the X-ray diagnostic apparatus 1 in the embodiment. As illustrated in FIG. 2, in the X-ray diagnostic apparatus 1, the controller 30 determines whether selection of the rotation imaging program has been received from the user (step S101).

When the controller 30 does not determine that the selection of the rotation imaging program has been received from the user (No at step S101), the controller 30 repeats the determination processing at step S101. By contrast, when the controller 30 determines that the selection of the rotation imaging program has been received from the user (Yes at step S101), the positioning unit 31 of the controller 30 executes the positioning processing (step S102). That is to say, the positioning unit 31 of the controller 30 makes the rotating center of the first imaging system and the rotating center of the second imaging system substantially identical to each other when a rotation imaging program using the first imaging system and the second imaging system is selected from the user. The processing procedures of the positioning processing performed by the positioning unit of the controller 30 will be described with reference to FIG. 3.

Figure 3:
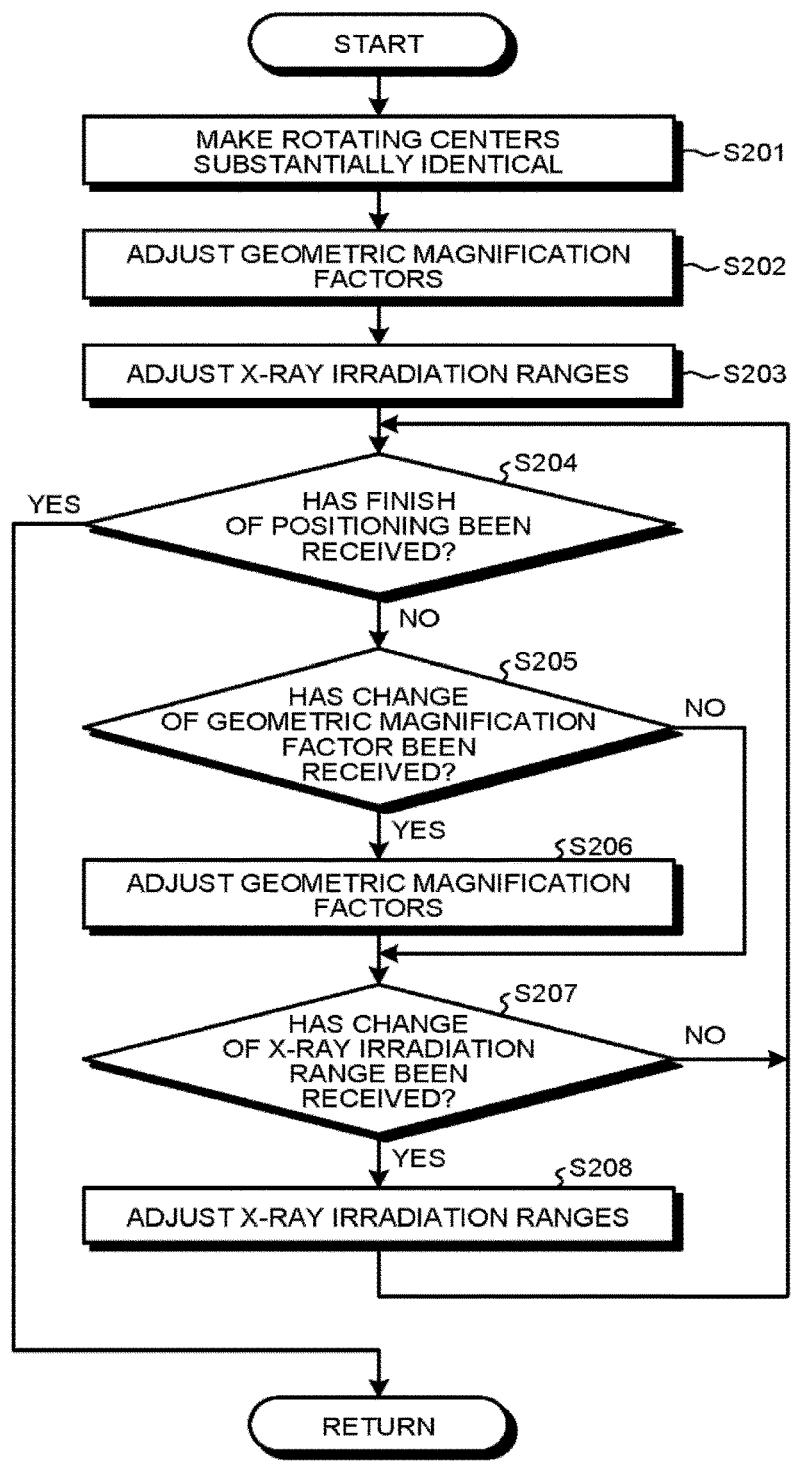
FIG. 3 is an exemplary flowchart illustrating processing procedures of positioning processing performed by a positioning unit of a controller in the first embodiment.
Figure 4:
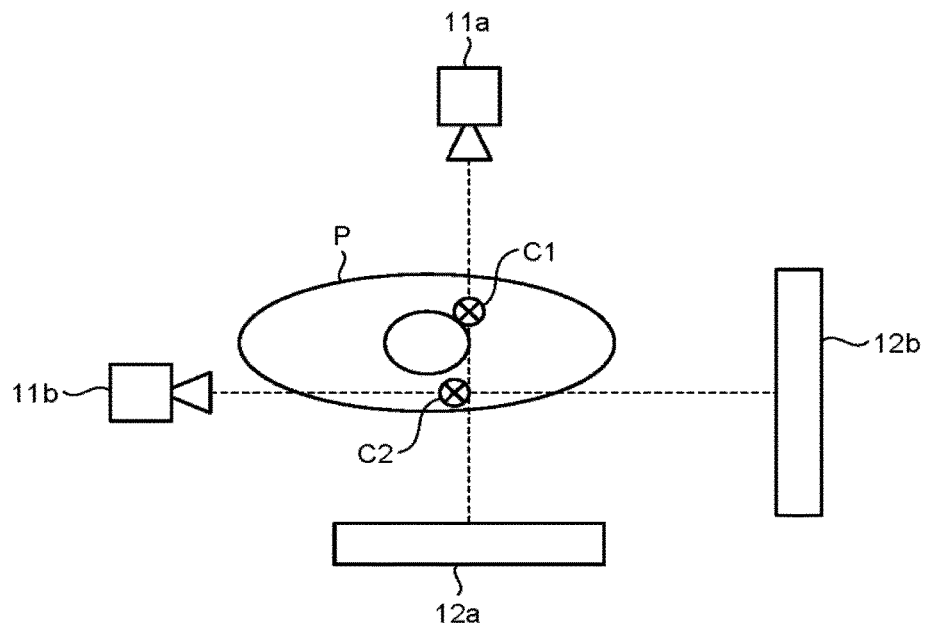
FIG. 4 is an exemplary first view for explaining the first embodiment.

FIG. 3 is a flowchart illustrating the processing procedures of the positioning processing performed by the positioning unit 31 of the controller 30 in the first embodiment. As illustrated in FIG. 3, the positioning unit 31 of the controller 30 makes the rotating center of the first imaging system and the rotating center of the second imaging system substantially identical to each other (step S201). The processing at step S201 will be described with reference to FIG. 4 and FIG. 5. FIG. 4 is a first view for explaining the first embodiment and FIG. 5 is a second view for explaining the first embodiment.

Figure 5:
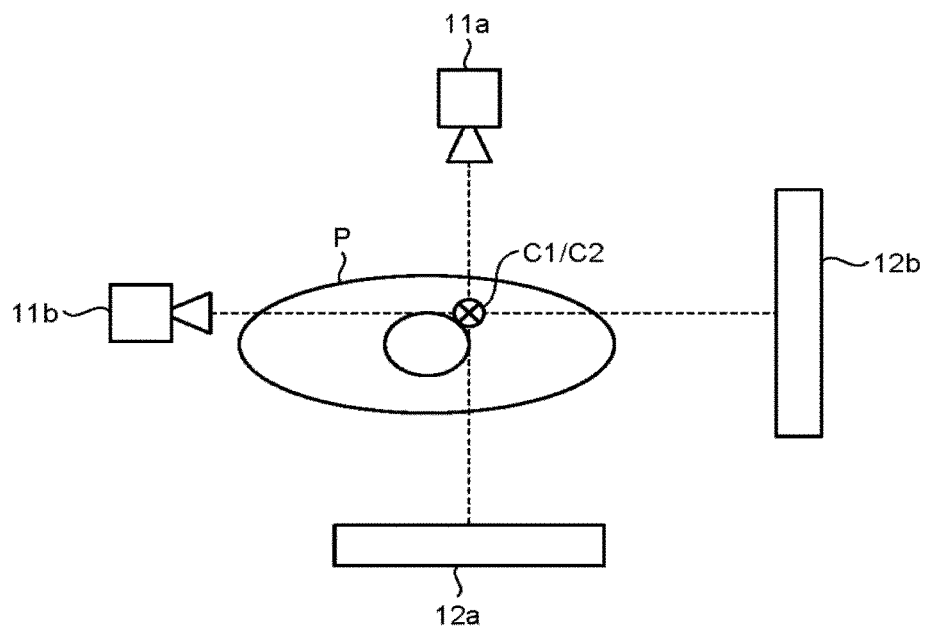
FIG. 5 is an exemplary second view for explaining the first embodiment.

FIG. 4 illustrates examples of the first imaging system and the second imaging system before the positioning processing and FIG. 5 illustrates examples of the first imaging system and the second imaging system after the positioning processing. FIG. 4 and FIG. 5 illustrate the subject P, the first imaging system, and the second imaging system.

In FIG. 4, a rotating center C1 of the first imaging system and a rotating center C2 of the second imaging system are not substantially identical to each other. In other words, the rotating center C1 of the first imaging system and the rotating center C2 of the second imaging system are separated. In this case, the positioning unit 31 of the controller 30 controls the second imaging system in the state as illustrated in FIG. 4 so as to make the rotating center C1 of the first imaging system and the rotating center C2 of the second imaging system substantially identical to each other as illustrated in FIG. 5. Although the positioning unit 31 of the controller 30 moves the second imaging system in the example as illustrated in FIG. 5, embodiments are not limited thereto. For example, the positioning unit 31 of the controller 30 may move the first imaging system so as to make the rotating center of the first imaging system and the rotating center of the second imaging system substantially identical to each other. Alternatively, the positioning unit 31 of the controller 30 may move both of the first imaging system and the second imaging system so as to make the rotating center of the first imaging system and the rotating center of the second imaging system substantially identical to each other. That is to say, when the user selects the rotation imaging program using the first imaging system and the second imaging system, in the case where the rotating center of the first imaging system and the rotating center of the second imaging system are not substantially identical to each other, the positioning unit 31 of the controller 30 controls at least either one of the first imaging system and the second imaging system so as to make the rotating center of the first imaging system and the rotating center of the second imaging system substantially identical to each other. It should be noted that the rotating center corresponds to the center of the imaging range. When the user selects the rotation imaging program using the first imaging system and the second imaging system, in the case where the rotating center C1 of the first imaging system and the rotating center C2 of the second imaging system are substantially identical to each other, the positioning unit 31 of the controller 30 may set movement amounts of the first imaging system and the second imaging system to zero so as to keep the rotating center C1 of the first imaging system and the rotating center C2 of the second imaging system substantially identical to each other.

Description is made with reference back to FIG. 3. Subsequently, the positioning unit 31 of the controller 30 further makes geometric magnification factors of a target at the rotating centers substantially identical between the first imaging system and the second imaging system (step S202). For example, the positioning unit 31 of the controller 30 adjusts a source to image-receptor distance (SID) between an X-ray focal point and an image reception surface for at least either one of the first imaging system and the second imaging system so as to make the geometric magnification factors of the target at the rotating centers substantially identical to each other.

As a more specific example, description is made for the case where a source to object distance (SOD: distance between the X-ray focal point and the rotating center in the vicinity of the center of the subject P) of the first imaging system is 650 mm, an SOD of the second imaging system is 700 mm, and the SID of the first imaging system is 1100 mm. In this case, if pixel pitches of the first X-ray detector and the second X-ray detector are substantially equal each other, the positioning unit 31 of the controller 30 adjusts the SID of the second imaging system to 1184.6 mm (=1100× 700/650). The positioning unit 31 of the controller 30 makes spatial resolutions of the X-ray images equivalent in this manner.

When pixel sizes of the detectors are different, the positioning unit 31 of the controller 30 controls the SID so as to make the resolutions at the rotating centers identical. As a more specific example, description is made for the case where a pixel size of the X-ray detector 12a of the first imaging system is 100 μm, a pixel size of the X-ray detector 12b of the second imaging system is 120 μm, the SOD of the first imaging system and the second imaging system is 700 mm, and the SID of the first imaging system is 1100 mm. In this case, the controller 30 adjusts the SID of the second imaging system to 1320 mm (=700×120×1100/(700×100)).

Figure 6:
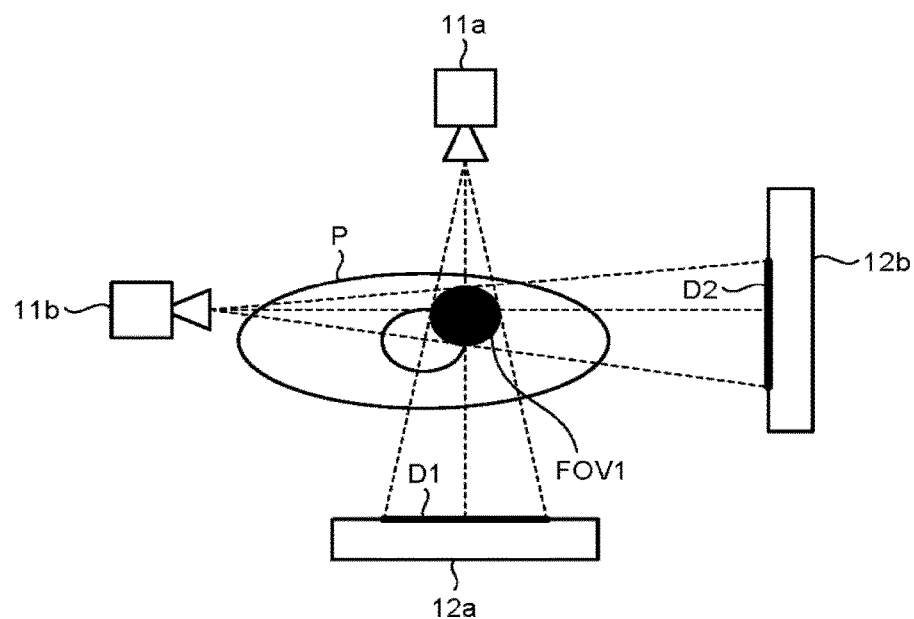
FIG. 6 is an exemplary third view for explaining the first embodiment.

The positioning unit 31 of the controller 30 further makes X-ray irradiation ranges substantially identical between the first imaging system and the second imaging system (step S203). For example, the positioning unit 31 of the controller 30 makes X-ray signal collection regions substantially identical between the first X-ray detector 12a and the second X-ray detector 12b. The processing at step S203 will be described with reference to FIG. 6. FIG. 6 is a third view for explaining the first embodiment.

In FIG. 6, the X-ray irradiation range onto the subject P is indicated by a black circle FOV1. The X-ray irradiation range is fluoroscopically checked from two views, one view with the first imaging system and another view with the second imaging system. Procedures of checking the irradiation range could be simplified because of substantially identical rotation centers between the first imaging system and the second imaging system. As illustrated in FIG. 6, the positioning unit 31 of the controller 30 adjusts the X-ray signal collection region of X-ray detector 12a of the first imaging system to D1 and adjusts the X-ray signal collection region of the X-ray detector 12b of the second imaging system to D2 so as to make the X-ray signal collection regions substantially identical between the first X-ray detector 12a and the second X-ray detector 12b. When matrix sizes of the first X-ray detector 12a and the second X-ray detector 12b are different from each other, the positioning unit 31 of the controller 30 further controls at least either one of the first X-ray detector 12a and the second X-ray detector 12b so as to make the matrix sizes substantially identical to each other. When X-ray focal point sizes of the first X-ray tube 11a and the second X-ray tube 11b are different from each other, the positioning unit 31 of the controller 30 further controls at least either one of the first X-ray tube 11a and the second X-ray tube 11b so as to make the X-ray focal point sizes substantially identical to each other.

Thereafter, the positioning unit 31 of the controller 30 determines whether finish of the positioning processing has been received (step S204). When the positioning unit 31 of the controller 30 determines that the finish of the positioning processing has been received (Yes at step S204), the positioning unit 31 finishes the positioning processing. By contrast, when the positioning unit 31 of the controller 30 does not determine that the finish of the positioning processing has been received (No at step S204), the positioning unit 31 determines whether change of the geometric magnification factor has been received (step S205).

When the positioning unit 31 of the controller 30 determines that the change of the geometric magnification factor has been received (Yes at step S205), the positioning unit 31 adjusts the geometric magnification factors (step S206). For example, when either one of the SID of the first imaging system and the SID of the second imaging system has been changed, the positioning unit 31 of the controller 30 adjusts the other one of the SIDs so as to make the geometric magnification factors of the target at the rotating centers substantially identical between the first imaging system and the second imaging system in the same manner as step S202.

Figure 7:
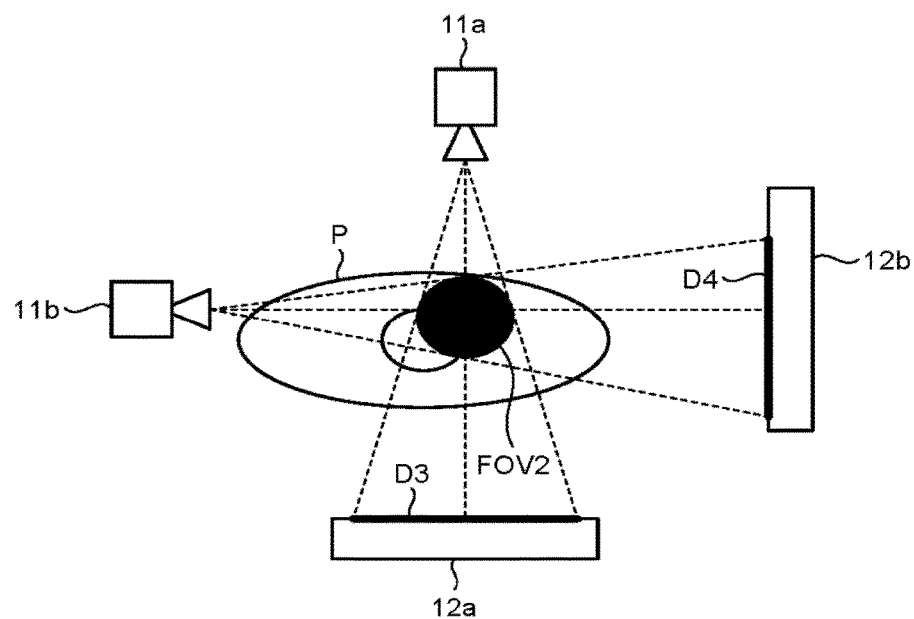
FIG. 7 is an exemplary fourth view for explaining the first embodiment.

After the positioning unit 31 of the controller 30 finishes the processing at step S206 or when the positioning unit 31 does not determine that the change of the geometric magnification factor has been received (No at step S205), the positioning unit 31 of the controller 30 determines whether change of the X-ray irradiation range has been received (step S207). When the positioning unit 31 of the controller 30 does not determine that the change of the X-ray irradiation range has been received (No at step S207), the positioning unit 31 returns the process to step S204. By contrast, when the positioning unit 31 of the controller 30 determines that the change of the X-ray irradiation range has been received (Yes at step S207), the positioning unit 31 adjusts the X-ray irradiation ranges (step S208). For example, when the X-ray signal collection region of the X-ray detector 12a of the first imaging system is changed, the positioning unit 31 of the controller 30 performs automatic switching so as to make the X-ray signal collection region of the X-ray detector 12b of the second imaging system identical to the X-ray signal collection region of the X-ray detector 12a of the first imaging system. The processing at step S208 will be described with reference to FIG. 7. FIG. 7 is a fourth view for explaining the first embodiment.

FIG. 7 illustrates the case where the X-ray irradiation range onto the subject P is changed to a black circle FOV2 from the black circle FOV1 as illustrated in FIG. 6. As illustrated in FIG. 7, the positioning unit 31 of the controller 30 adjusts the X-ray signal collection region of X-ray detector 12a of the first imaging system to D3 and adjusts the X-ray signal collection region of the X-ray detector 12b of the second imaging system to D4 so as to make the X-ray signal collection regions substantially identical between the first X-ray detector 12a and the second X-ray detector 12b.

For example, when the matrix size of the X-ray detector 12a of the first imaging system is changed, the positioning unit 31 of the controller 30 automatically changes the matrix size of the X-ray detector 12b of the second imaging system to the matrix size identical to that of the X-ray detector 12a of the first imaging system. In the same manner, when the matrix size of the X-ray detector 12b of the second imaging system is changed, the positioning unit 31 of the controller 30 automatically changes the matrix size of the X-ray detector 12a of the first imaging system to the matrix size identical to that of the X-ray detector 12b of the second imaging system.

The positioning unit 31 of the controller 30 controls collection pixel sizes in the same manner. To be more specific, when the collection pixel size of the X-ray detector 12a of the first imaging system is changed, the positioning unit 31 of the controller 30 controls the matrix size of the X-ray detector 12b of the second imaging system and performs automatic switching so as to make the collection pixel sizes identical between the X-ray detector 12a of the first imaging system and the X-ray detector 12b of the second imaging system. In the same manner, when the collection pixel size of the X-ray detector 12b of the second imaging system is changed, the positioning unit 31 of the controller 30 controls the matrix size of the X-ray detector 12a of the first imaging system and performs automatic switching so as to make the collection pixel sizes identical between the X-ray detector 12a of the first imaging system and the X-ray detector 12b of the second imaging system.

Furthermore, when the X-ray focal point size of the first X-ray tube 11a is changed, the positioning unit 31 of the controller 30 controls the X-ray focal point size of the second X-ray tube 11b so as to make the X-ray focal point sizes substantially identical between the first X-ray tube 11a and the second X-ray tube 11b. In the same manner, when the X-ray focal point size of the second X-ray tube 11b is changed, the positioning unit 31 of the controller 30 controls the X-ray focal point size of the first X-ray tube 11a so as to make the X-ray focal point sizes substantially identical between the first X-ray tube 11a and the second X-ray tube 11b.

Description is made with reference back to FIG. 2. When the positioning processing at step S102 is completed, the controller 30 determines whether start of the rotation imaging has been received (step S103). For example, the controller 30 determines whether an imaging switch has been pressed. When the controller 30 does not determine that the start of the rotation imaging has been received (No at step S103), the controller 30 repeats the determination processing at step S103. By contrast, when the controller 30 determines that the imaging switch has been pressed and the start of the rotation imaging has been received (Yes at step S103), the controller 30 moves forward to step S104 and starts imaging.

Before the rotation imaging is started, the following processing is performed as preparation for the rotation imaging, for example. The medical doctor slowly rotates the individual arms to the rotation start angles from the rotation end angles in order to confirm that the arms do not make contact with the subject P and couch 14 during the rotation by the rotation imaging. Then, when the arms stop at the rotation start angles, the medical doctor then prepares the injector 50 and connects the injector 50 to the catheter. Furthermore, the medical doctor sets the imaging conditions. The preparation for the imaging is completed with completion of the preparation of the injector 50 and so on.

In the X-ray diagnostic apparatus 1, the X-ray imaging mechanism 10 collects the mask images by biplanes under control by the controller 30 (step S104). First, for example, the first imaging system rotates by 0 degree to 100 degrees and the second imaging system rotates by −100 degrees to 0 degree simultaneously. For example, 100 pieces of data are collected at an interval of a substantially equal angle during the rotation.

After the mask images are collected, the X-ray diagnostic apparatus 1 rotates the first imaging system and the second imaging system in the opposite directions and returns the first imaging system and the second imaging system to respective start positions (step S105).

When the first imaging system and the second imaging system return to the respective start positions, the X-ray diagnostic apparatus 1 transmits a driving signal to the injector 50 and the contrast agent is injected into the subject P (step S106). For example, the injector 50 injects the contrast agent into the subject P for three seconds at 2 to 3 (cc/sec).

Subsequently, the X-ray diagnostic apparatus 1 determines whether a predetermined period of time has passed (step S107). When the X-ray diagnostic apparatus 1 does not determine that the predetermined period of time has passed (No at step S107), the X-ray diagnostic apparatus 1 repeats the determination processing until the predetermined period of time passes. The predetermined period of time is time until the contrast agent reaches to region of interest and is approximately 1 second in this example.

When the X-ray diagnostic apparatus 1 determines that the predetermined period of time has passed (Yes at step S107), the X-ray imaging mechanism 10 collects the contrast images by biplanes under control by the controller 30 (step S108). For example, after the injection of the contrast agent, the X-ray diagnostic apparatus 1 rotates the first imaging system and the second imaging system in the forward directions and collects pieces of image data in the same manner as the imaging at step S104.

The X-ray diagnostic apparatus 1 once stores the pieces of collected image data in the image memory 22 when the imaging is completed (step S109). When the pieces of image data are accumulated in the image memory 22, the mask images and the contrast images are transferred to the subtraction unit 23.

Then, the subtraction unit 23 performs subtraction of the mask images (pieces of projection data) and the contrast images (pieces of projection data) at the approximately same angles (step S110). DSA images generated by the subtraction are transmitted to the three-dimensional reconstruction unit 29.

The three-dimensional reconstruction unit 29 reconstructs a three-dimensional volume image from the pieces of DSA images (step S111). That is to say, the three-dimensional reconstruction unit 29 reconstructs the three-dimensional image from the first X-ray images that are sequentially generated by the first X-ray detector 12a and the second X-ray images that are sequentially generated by the second X-ray detector 12b. As an example of a reconstruction method, a filtered back projection method proposed by Feldkamp et al. is used. The three-dimensional reconstruction unit 29 applies an appropriate convolution filter such as Shepp&Logan and Ramachandran to the DSA images of 200 frames. Then, the three-dimensional reconstruction unit 29 performs back projection operation so as to provide the reconstructed data.

The reconstruction region is defined as a cylinder inscribed in an X-ray flux from the X-ray tube in the entire directions. For example, an inner portion of the cylinder needs to be discretized three-dimensionally by a length d on a center portion of the reconstruction region that is projected onto a width of one detecting element of the X-ray detector and reconstruction images of pieces of data at discretization points need to be provided. Although an example of a discretization interval is described, the interval may be different depending on apparatuses and manufacturers. It is sufficient that the discretization interval defined for the individual apparatus is used in principle. Although the three-dimensional image is reconstructed by a direct reconstruction method in this example, the three-dimensional reconstruction unit 29 may reconstruct the three-dimensional image by an iterative approximation reconstruction method. The reconstructed three-dimensional image is transmitted to the three-dimensional image processor 25.

After the three-dimensional reconstruction unit 29 reconstructs the three-dimensional image in the above-described manner, the X-ray diagnostic apparatus 1 sequentially generates fluoroscopic images by the first imaging system and the second imaging system. The three-dimensional image processor 25 generates three dimensional vascular images projected from the positions of the first imaging system and the second imaging system at the current time based on the three-dimensional image reconstructed by the three-dimensional reconstruction unit 29. The three-dimensional image processor 25 generates a volume rendering image, a projection image, an MIP image, or the like as the three dimensional vascular image. Then, the three-dimensional image processor 25 generates the three-dimensional roadmap image by superimposing the generated three dimensional vascular image and the fluoroscopic images that are provided in real time and causes the display unit 40 to display the three-dimensional roadmap image. The medical doctor can therefore control the catheter and the guide wire while recognizing whether the blood vessel into which the medical doctor tries to insert the catheter and the guide wire runs to the front side or the deep side. As a result, the medical doctor can insert the catheter and the guide wire in a short period of time.

As described above, the X-ray diagnostic apparatus 1 in the first embodiment makes the rotating centers of the first imaging system and the second imaging system, for which the rotation is controlled independently, substantially identical to each other. With this process, the medical doctor can check the target region at two views, one with the first imaging system and another with the second imaging system. For example, the medical doctor can perform relative positioning between the imaging systems and the subject P simply by setting the first imaging system in front of the subject P and setting the second imaging system along the side of the subject P and confirming that a target region is located in the vicinity of the center of the field of view. The medical doctor can therefore simplify the positioning operation of the subject P.

In the above-described first embodiment, the X-ray diagnostic apparatus 1 can eliminate complicated procedures to adjust relative positioning of the subject P, the first imaging system and the second imaging system. With this advantage, the medical doctor can observe the three-dimensional image in a shorter period of time with less effort than conventional procedures.

In the conventional three dimensional imaging, the injector 50 has been used because an amount of the contrast agent is limited when the contrast agent is injected by a syringe or other devices. For example, it takes approximately 4.5 seconds to 5 seconds to collect the X-ray images with presence of the contrast agent whereas only the contrast agent can be injected by the syringe for approximately 3 seconds. That is to say, when the contrast agent is injected by the syringe or other devices, the contrast agent is not enough to perform existing three dimensional imaging. By contrast, in the first embodiment, the rotation imaging is performed with the first imaging system and the second imaging system, so that injection time is equal to or less than 3 seconds. In this case, the operation of moving injector 50 to the vicinity of the couch 14, the operation of connecting the catheter to the injector 50, the operation of setting the injection conditions on the injector 50, the operation of disconnecting the catheter from the injector 50, and the operation of moving the injector 50 away from the couch 14 are further eliminated. As a result, the manipulation time can be further shortened.

Second Embodiment

In the above-described first embodiment, the three-dimensional image is reconstructed while the positioning processing performed by the positioning unit 31 of the controller 30 makes the spatial resolutions substantially equivalent between the first imaging system and the second imaging system. In the positioning processing, the spatial resolutions cannot be made substantially equivalent in some cases. In a second embodiment, pieces of processing that are executed when the positioning processing performed by the positioning unit 31 of the controller 30 cannot make the spatial resolutions substantially equivalent.

For example, it is assumed that the matrix size of the X-ray detector 12a of the first imaging system and the matrix size of the X-ray detector 12b of the second imaging system are 1024×1024 and the size of each pixel is 100 μm. For the convenience of explanation, an X-ray optical system in which the SOD of the first imaging system is 600 mm, the SID thereof is 1200 mm, the SOD of the second imaging system is 300 mm, and the SID thereof is 1200 mm is used, as an example. In this case, the X-ray magnification factor of the second imaging system is twice as big as the X-ray magnification factor of the first imaging system. The X-ray images from the second imaging system enable observation of fine structures in extremely narrow ranges. By contrast, the X-ray images from the first imaging system of worse spatial resolution in wider ranges than those from the second imaging system. When the geometric magnification factors are substantially equivalent between the first imaging system and the second imaging system, for a back projection trajectory from a certain angle θ, air region behind anatomical structures on the back projection structures gets certain values by the back projection calculation. But the values are cancelled out by the back projection calculation from certain range of angle (θ+90) or (θ−90). When the geometric magnification factors are not substantially equivalent between the first imaging system and the second imaging system, the values are not cancelled out as expected and remain as artifacts.

Figure 8A:
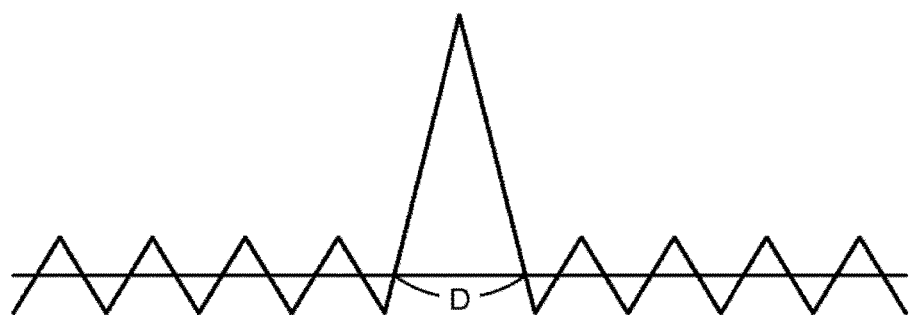
FIG. 8A is an exemplary first view for explaining a second embodiment.

When the geometric magnification factors of the target at the rotating centers are not substantially equivalent between the first imaging system and the second imaging system, the three-dimensional reconstruction unit 29 reconstructs the three-dimensional image using spatial filters (reconstruction kernels) for making the spatial resolutions of the target equivalent to each other. FIG. 8A is a first view for explaining the second embodiment and FIG. 8B is a second view for explaining the second embodiment, where D shows pixel pitch of an X-ray detector 12a and an X-ray detector 12b.

Figure 8B:
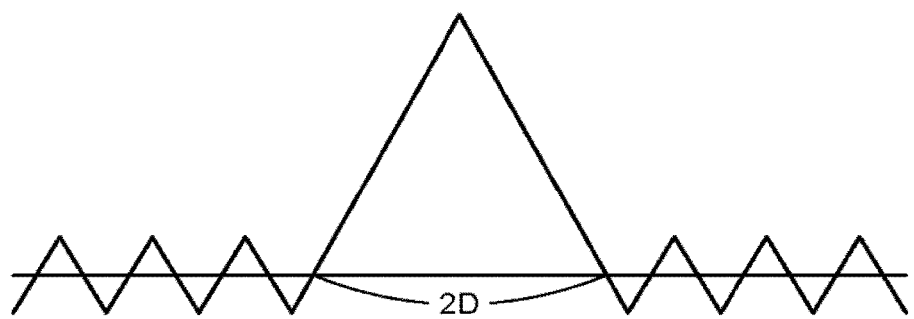
FIG. 8B is an exemplary second view for explaining the second embodiment.

FIG. 8A illustrates an example of the reconstruction kernels for the images collected by the first imaging system and FIG. 8B illustrates an example of the reconstruction kernels for the images collected by the second imaging system. In FIG. 8A and FIG. 8B, the X-ray magnification factor of the second imaging system is twice as big as the X-ray magnification factor of the first imaging system.

For example, as illustrated in FIG. 8A and FIG. 8B, the three-dimensional reconstruction unit 29 reconstructs the three-dimensional image using the different reconstruction kernels for the images collected by the first imaging system and the reconstruction kernels for the images collected by the second imaging system so as to make the spatial resolution of the target at the rotating centers substantially equivalent to each other. The three-dimensional reconstruction unit 29 can therefore prevent remaining of the artifacts that is generated due to the difference in the spatial resolution of the target at the rotating center.

The three-dimensional reconstruction unit 29 may reconstruct the three-dimensional image after filtering processing of making the spatial resolutions of the target equivalent. For example, the three-dimensional reconstruction unit 29 reconstructs the three-dimensional image by the direct reconstruction method after weakened high-pass filtering processing is performed, in preprocessing, on the collected images from the second imaging system so as to make spatial resolution substantially equivalent.

First Modification of Second Embodiment

Figure 9:
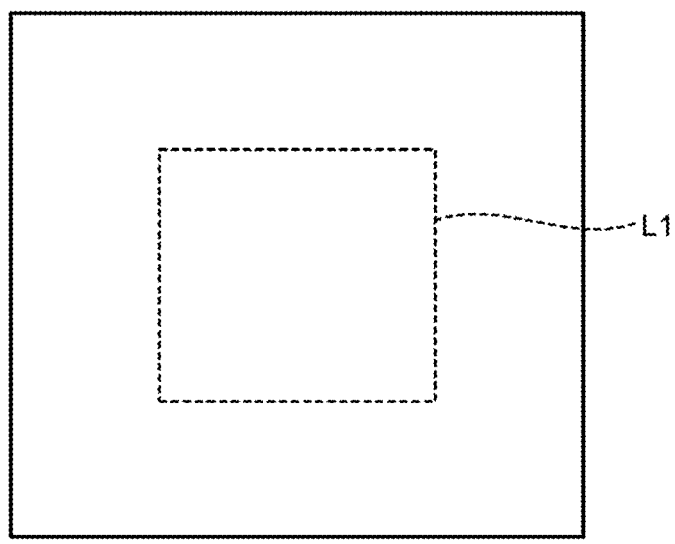
FIG. 9 is an exemplary view for explaining a first modification of the second embodiment.

Furthermore, when at least either one of the geometric magnification factors of the target at the rotating centers and the X-ray signal collection regions are not substantially equivalent between the first imaging system and the second imaging system, the positioning unit 31 of the controller 30 displays the X-ray image with information indicating the reconstruction region based on the X-ray signal collection region of the first imaging system and the second imaging system on the display unit 40. FIG. 9 is a view for explaining a first modification of the second embodiment. FIG. 9 illustrates the case where information indicating the reconstruction region is narrower than collection region of the first imaging system. As illustrated in FIG. 9, the positioning unit 31 of the controller 30 controls to display a guide line L1 indicating the reconstruction region on the collection images from the first imaging system because the reconstruction region is narrow due to the collection images from the second imaging system.

Second Modification of Second Embodiment

Figure 10:
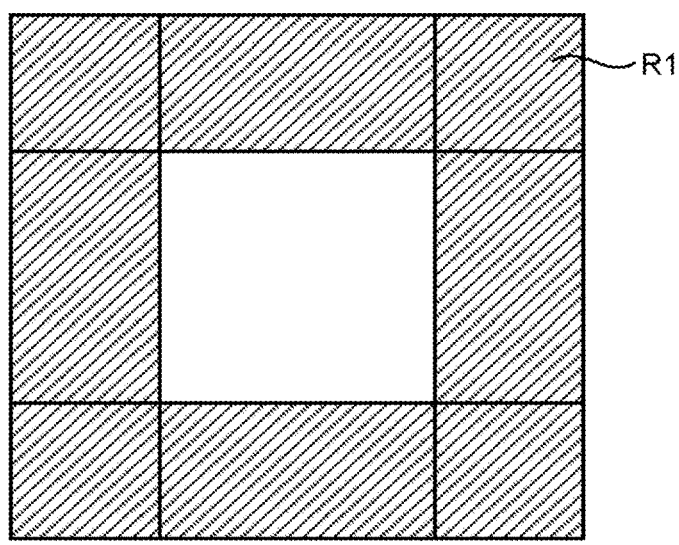
FIG. 10 is an exemplary view for explaining a second modification of the second embodiment.

Alternatively, when at least either one of the geometric magnification factors of the target at the rotating centers and the X-ray signal collection regions are not substantially equivalent between the first imaging system and the second imaging system, the positioning unit 31 of the controller 30 may control collimators so that the first imaging system and the second imaging system covers the reconstruction region appropriately. The collimator is a slit for narrowing the X-ray irradiation range. The X-ray filter is a filter for adjusting the X-ray spectrum exposed from the X-ray tube 11a or the X-ray tube 11b. FIG. 10 is a view for explaining a second modification of the second embodiment. FIG. 10 illustrates the case where the reconstruction region is narrower than the collection region of the first imaging system. As illustrated in FIG. 10, the positioning unit 31 of the controller 30 adjusts an aperture of the collimator so as to adjust the X-ray irradiation range (fan angle and cone angle) and shield a region R1 other than the reconstruction region.

Other Embodiments

Embodiments are not limited to the above-described embodiments.

In the description of the above-described embodiments, the components of the devices as illustrated in the drawings are conceptual functionally and are not necessarily required to be configured as illustrated in the drawings physically. That is to say, specific forms of distribution and integration of the devices are not limited to those as illustrated in the drawings, and all of or a part of the devices can be configured to be distributed or integrated functionally or physically based on a desired unit depending on various loads and usage conditions. Furthermore, all of or any part of processing functions operating in the devices can be implemented by a central processing unit (CPU) and a computer program that is analyzed and executed by the CPU or can be implemented as hardware by a wired logic.

A control method as described in the above-described embodiments can be also implemented by executing a previously prepared control program by a computer such as a personal computer and a workstation. The control program can be distributed through a network such as the Internet. The control program can be also executed by being recorded in a computer readable recording medium such as a hard disk, a flexible disk (FD), a compact disc read only memory (CD-ROM), a magnetooptic disc (MO), and a digital versatile disc (DVD) and being read from the recording medium by the computer.

Figure 11:
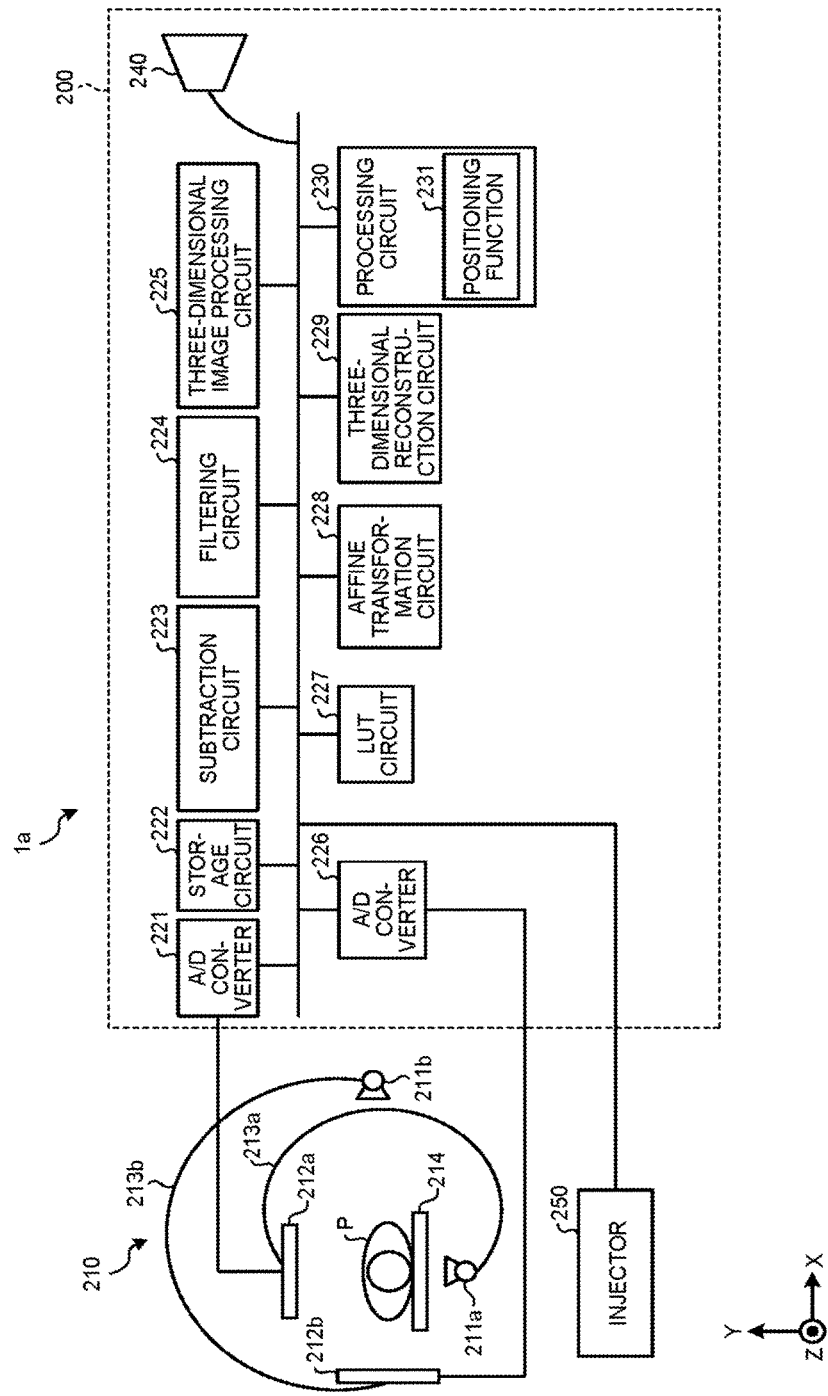
FIG. 11 is an exemplary diagram illustrating an example of the configuration of an X-ray diagnostic apparatus according to another embodiment.

The X-ray diagnostic apparatus as illustrated in the drawings in the description of the first and second embodiments may be configured as illustrated in FIG. 11, for example. FIG. 11 is a diagram illustrating an example of the configuration of an X-ray diagnostic apparatus 1a according to another embodiment.

As illustrated in FIG. 11, the X-ray diagnostic apparatus 1a in another embodiment includes an X-ray imaging mechanism 210 and an image processing device 200. The X-ray imaging mechanism 210 and the image processing device 200 correspond to the X-ray imaging mechanism 10 and the image processing device 100 as illustrated in FIG. 1, respectively.

The X-ray imaging mechanism 210 is a biplane imaging mechanism including a first imaging system and a second imaging system as illustrated in FIG. 11. The first imaging system includes an X-ray tube 211a, an X-ray detector 212a, and a C-shaped arm 213a and the second imaging system includes an X-ray tube 211b, an X-ray detector 212b, and an Ω-shaped arm 213b. The X-ray tube 211a, the X-ray detector 212a, the C-shaped arm 213a, the X-ray tube 211b, the X-ray detector 212b, and the Ω-shaped arm 213b as illustrated in FIG. 11 correspond to the X-ray tube 11a, the X-ray detector 12a, the C-shaped arm 13a, the X-ray tube 11b, the X-ray detector 12b, and the Ω-shaped arm 13b as illustrated in FIG. 1, respectively.

The X-ray imaging mechanism 210 includes a couch 214 and an injector 250 is connected thereto. The couch 214 and the injector 250 as illustrated in FIG. 11 correspond to the couch 14 and the injector 50 as illustrated in FIG. 1, respectively.

As illustrated in FIG. 11, the image processing device 200 includes an A/D converter 221, storage circuitry 222, subtraction circuitry 223, filtering circuitry 224, three-dimensional image processing circuitry 225, an A/D converter 226, LUT circuitry 227, affine transformation circuitry 228, three-dimensional reconstruction circuitry 229, processing circuitry 230, and a display 240.

The A/D converter 221 corresponds to the A/D converter 21 as illustrated in FIG. 1 and the storage circuitry 222 corresponds to the image memory 22 as illustrated in FIG. 1. The subtraction circuitry 223 corresponds to the subtraction unit 23 as illustrated in FIG. 1 and executes the processing at step S110 as illustrated in FIG. 2. The filtering circuitry 224, the three-dimensional image processing circuitry 225, the A/D converter 226, the LUT circuitry 227, the affine transformation circuitry 228, and the display 240 correspond to the filtering unit 24, the three-dimensional image processor 25, the A/D converter 26, the LUT 27, the affine transformation unit 28, and the display unit 40 as illustrated in FIG. 1, respectively. The three-dimensional reconstruction circuitry 229 corresponds to the three-dimensional reconstruction unit 29 as illustrated in FIG. 1 and executes the processing at step S111 as illustrated in FIG. 2. The three-dimensional reconstruction circuitry 229 in another embodiment is an example of a reconstruction circuitry in the scope of the invention.

The processing circuitry 230 corresponds to the controller 30 as illustrated in FIG. 1. The processing circuitry 230 activates a positioning function 231 to operate when a user selects a rotation imaging program. For example, the processing circuitry 230 makes the rotating center of the first imaging system and the rotating center of the second imaging system substantially equivalent to each other. The positioning function 231 works similarly with the positioning unit 31 as illustrated in FIG. 1. The processing circuitry 230 is an example of a processing circuitry in the scope of the invention.

For example, a processing function that is implemented as a component on the processing circuitry 230 as illustrated in FIG. 11 is recorded in the storage circuitry 222 in a form of a computer executable program. The processing circuitry 230 is a processor that reads the computer programs from the storage circuitry 222 and executes the computer programs so as to activate the functions corresponding to the programs to operate. In other words, the processing circuitry 230 that has read the computer programs has the positioning function 231 as illustrated in the processing circuitry 230 of FIG. 11. That is to say, the processing circuitry 230 reads the computer program corresponding to the positioning function 231 from the storage circuitry 222 and executes the computer program so as to execute the same processing of the positioning unit 31.

For example, the processing circuitry 230 calls the computer program corresponding to the positioning function 231 from the storage circuitry 222 and executes the computer program, so that the pieces of processing at step S201 to step S208 as illustrated in FIG. 3 are executed.

Although the single processing circuitry 230 executes the processing functions that are accomplished by the positioning function 231 in FIG. 11, a plurality of independent processors may be combined to configure a processing circuitry and these processors may execute the computer programs so as to activate the corresponding functions to operate.

The word "processor" used in the description above indicates a central processing unit (CPU), a graphics processing unit (GPU), or a circuitry such as an application specific integrated circuit (ASIC) and a programmable logic device (for example, a simple programmable logic device (SPLD), a complex programmable logic device (CPLD), and a field programmable gate array (FPGA)). The processors read the computer programs stored in the storage circuitry and execute the computer programs so as to activate the corresponding functions to operate. Instead of storage of the computer programs in the storage circuitry, the computer programs may be directly incorporated on circuits of the processors. In this case, the processors read the computer programs incorporated in the circuits and execute the computer programs so as to activate the corresponding functions to operate. The processors in the embodiment are not limited to be configured as single circuits for the respective processors. A plurality of independent circuits may be combined to configure one processor and the processor may activate functions thereof to operate. The components in FIG. 11 may be integrated into one processor and the processor may activate the functions thereof to operate.

According to at least one of the above-described embodiments, rotation imaging using the first imaging system and the second imaging system can be realized with simpler configurations.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus, comprising:
a first imaging system configured to hold a first X-ray tube and a first X-ray detector in a rotatable manner, the first imaging system having a first rotating center;
a second imaging system configured to hold a second X-ray tube and a second X-ray detector in a rotatable manner, the second imaging system having a second rotating center, the first and second rotating centers being set independently, for the first imaging system and the second imaging system; and
processing circuitry configured to make the first rotating center and the second rotating center substantially equivalent to each other, when a rotation imaging program using the first imaging system and the second imaging system is executed.

2. The X-ray diagnostic apparatus according to claim 1, wherein when the rotation imaging program using the first imaging system and the second imaging system is selected, when the rotating center of the first imaging system and the rotating center of the second imaging system are not substantially equivalent to each other, the processing circuitry is configured to control at least either one of the first imaging system and the second imaging system so as to make the rotating center of the first imaging system and the rotating center of the second imaging system substantially equivalent to each other.

3. The X-ray diagnostic apparatus according to claim 1, wherein the processing circuitry is configured to make geometric magnification factors of a target at the rotating centers substantially equivalent between the first imaging system and the second imaging system.

4. The X-ray diagnostic apparatus according to claim 2, wherein the processing circuitry is further configured to make geometric magnification factors of a target at the rotating centers substantially equivalent between the first imaging system and the second imaging system.

5. The X-ray diagnostic apparatus according to claim 1, wherein the processing circuitry is further configured to make geometric magnification factors of a target at the rotating centers substantially equivalent to each other by adjusting a distance between an X-ray focal point and an image reception surface for at least one of the first imaging system and the second imaging system.

6. The X-ray diagnostic apparatus according to claim 2, wherein the processing circuitry is further configured to make geometric magnification factors of a target at the rotating centers substantially equivalent to each other by adjusting a distance between an X-ray focal point and an image reception surface for at least either one of the first imaging system and the second imaging system.

7. The X-ray diagnostic apparatus according to claim 1, wherein the processing circuitry is further configured to adjust X-ray signal collection regions so as to cover a reconstruction region appropriately between the first X-ray detector and the second X-ray detector.

8. The X-ray diagnostic apparatus according to claim 2, wherein the processing circuitry is further configured to adjust X-ray signal collection regions so as to cover a reconstruction region appropriately between the first X-ray detector and the second X-ray detector.

9. The X-ray diagnostic apparatus according to claim 1, wherein the processing circuitry is further configured to make geometric magnification factors of a target at the rotating centers substantially equivalent between the first X-ray detector and the second X-ray detector.

10. The X-ray diagnostic apparatus according to claim 2, wherein the processing circuitry is further configured to make geometric magnification factors of a target at the rotating centers substantially equivalent between the first X-ray detector and the second X-ray detector.

11. The X-ray diagnostic apparatus according to claim 1, wherein the processing circuitry is further configured to make pixel pitches substantially equivalent between the first X-ray detector and the second X-ray detector.

12. The X-ray diagnostic apparatus according to claim 2, wherein the processing circuitry is further configured to make pixel pitches substantially equivalent between the first X-ray detector and the second X-ray detector.

13. The X-ray diagnostic apparatus according to claim 1, wherein the processing circuitry is further configured to make X-ray focal point sizes substantially equivalent between the first X-ray tube and the second X-ray tube.

14. The X-ray diagnostic apparatus according to claim 2, wherein the processing circuitry is further configured to make X-ray focal point sizes substantially equivalent between the first X-ray tube and the second X-ray tube.

15. The X-ray diagnostic apparatus according to claim 1, further comprising reconstruction circuitry configured to reconstruct a three-dimensional image using first X-ray images that are sequentially generated based on X-ray signals collected by the first X-ray detector and second X-ray images that are sequentially generated based on X-ray signals collected by the second X-ray detector.

16. The X-ray diagnostic apparatus according to claim 15, wherein when geometric magnification factors of a target at the rotating centers are not substantially equivalent between the first imaging system and the second imaging system, the reconstruction circuitry reconstructs the three-dimensional image after performing filtering processing to make spatial resolutions of the target equivalent or reconstructs the three-dimensional image using a filter to make the spatial resolutions of the target equivalent.

17. The X-ray diagnostic apparatus according to claim 16, wherein when at least one of the geometric magnification factors of the target at the rotating centers and X-ray signal collection regions are not substantially equivalent between the first imaging system and the second imaging system, the processing circuitry is configured to cause a display to display an X-ray image with information indicating a reconstruction region of a reconstruction region on the display.

18. The X-ray diagnostic apparatus according to claim 16, wherein when at least one of the geometric magnification factors of the target at the rotating centers and X-ray signal collection regions are not substantially equivalent between the first imaging system and the second imaging system, the processing circuitry is configured to control a collimator so as to cover reconstruction regions appropriately between the first imaging system and the second imaging system.

19. The X-ray diagnostic apparatus according to claim 1, wherein the processing circuitry is further configured to move the first imaging system to a front of a subject and move the second imaging system to a side of the subject with making the rotating center of the first imaging system and the rotating center of the second imaging system substantially equivalent to each other.

20. The X-ray diagnostic apparatus of claim 1, wherein the processing circuitry is configured to make the first and second rotating centers substantially equivalent to each other when the rotation imaging program, which is for acquiring a three-dimensional image, is executed.

* * * * *